United States Patent [19]
Stock

[11] Patent Number: 6,150,177
[45] Date of Patent: Nov. 21, 2000

[54] DEVICE AND PROCESS FOR DETERMINING THE TEMPERATURE OF THE GAS SAMPLE FLOW DURING BREATH ALCOHOL MEASUREMENTS

[75] Inventor: Burkhard Stock, Lübeck, Germany

[73] Assignee: Dräger Sicherheitstechnik GmbH, Germany

[21] Appl. No.: 09/132,948

[22] Filed: Aug. 11, 1998

[30] Foreign Application Priority Data

Mar. 14, 1998 [DE] Germany .................. 198 11 177

[51] Int. Cl.⁷ .................................................. G01N 33/48
[52] U.S. Cl. .......................... 436/132; 436/900; 422/84; 73/23.3
[58] Field of Search ................ 422/83–87; 436/132, 436/900; 73/23.3

[56] References Cited

U.S. PATENT DOCUMENTS 4,809,810  3/1989  Elfman et al. .................. 180/272

OTHER PUBLICATIONS

Schoknecht et al. Aug. 13–18, 1995 The Technical Concept for Evidential Breath Testing in Germany Alcohol, Drugs and Traffic Safety—T'95, vol. 1.

*Primary Examiner*—Lyle A. Alexander
*Attorney, Agent, or Firm*—McGlew and Tuttle, P.C.

[57] ABSTRACT

A device comprising a combination of a mouthpiece (2) with a holder (1), which receives the mouthpiece (2) and has a sampling channel (4) leading to a breath alcohol-measuring device and a temperature sensor (11) arranged in the connection area between the holder (1) and the mouthpiece (2). To make it possible to determine the temperature of the mouthpiece (2) inserted into the holder (1) the mouthpiece (2) is designed for the temperature sensor (11) to be arranged in the sampling channel (4) as a wall section (10) covering the inner wall of the sampling channel (4) in the area of the temperature sensor (11).

10 Claims, 4 Drawing Sheets

DEVICE AND PROCESS FOR DETERMINING THE TEMPERATURE OF THE GAS SAMPLE FLOW DURING BREATH ALCOHOL MEASUREMENTS

FIELD OF THE INVENTION

The present invention pertains to a device and a process based on a combination of a mouthpiece with a holder, which receives the mouthpiece and has a sampling channel leading to a breath alcohol-measuring device and a temperature sensor arranged in a connection area between the holder and the mouthpiece.

BACKGROUND OF THE INVENTION

Accurate determination of the temperature of the gas sample blown by the subject into the measuring device is necessary for the measurement of the breath alcohol concentration. However, the temperature sensor cannot be introduced directly into the area of the mouth of the subject for hygienic and application technical reasons. It is located, instead, behind a replaceable mouthpiece, which is inserted into a heated holder on the measuring device. To avoid condensation effects of the gas sample, which is saturated with moisture, within the holder, the holder and usually also the components arranged downstream are heated to a temperature of about 39° C.

A mouthpiece, into which the subject blows, is inserted into the holder before the beginning of the measurement. Since a plurality of measurements are normally performed with different subjects in a rapid succession, the mouthpiece is inserted into the holder only shortly before the measurement. The temperature of the mouthpiece is normally at the ambient temperature level before use, and this temperature level is subject to great variations depending on the place of use and the time of the year. If the mouthpiece has not completely assumed the temperature of the holder before the measurement, the temperature measurement is distorted, because the breath gas sample is cooled by the mouthpiece during the blowing into the breath alcohol-measuring device. Since it is, on the other hand, impossible to wait until a stable temperature gradient has become established between the mouthpiece and the heated holder, knowledge of the temperature of the mouthpiece at the time of insertion into the holder is necessary.

A sampling device of a breath alcohol-measuring device, in which a mouthpiece is inserted into a preheated holder, has been known from the publication "Schonknecht, G. and B. Stock: The Technical Concept for Evidential Breath Testing in Germany", 13th International Conference on Alcohol, Drugs and Traffic Safety, Adelaide, Aug. 13 through Aug. 18, 1995. However, the temperature sensor is located in a sampling channel, which is surrounded by the wall of the holder. When the mouthpiece is pushed into the holder, the temperature at the temperature sensor changes but slightly, because the temperature sensor is shielded from the mouthpiece by the wall of the sampling channel. The effect of the storage temperature of the mouthpiece on the temperature measurement of the gas sample flow has hitherto been underestimated, because the mouthpiece has a very small mass and, on the other hand, it also has a length of only a few cm. However, more recent investigations have shown that the accuracy of measurement can be markedly increased by taking into account the temperature of the mouthpiece during the breath alcohol analysis.

SUMMARY AND OBJECTS OF THE INVENTION

The primary object of the present invention is to improve a device of this type such that the determination of the temperature of a mouthpiece inserted into a holder of a breath alcohol-measuring device is possible.

According to the invention a combination is provided of a mouthpiece with a holder that receives the mouthpiece and has a sampling channel leading to a breath alcohol-measuring device and a temperature sensor arranged in a connection area between the holder and the mouthpiece. The mouthpiece is designed for the temperature sensor to be arranged in the sampling channel as a wall section covering the inner wall of the sampling channel at least partially in the area of the temperature sensor.

According to a further aspect of the invention, a combination of a mouthpiece with a holder is provided which receives the mouthpiece and has a sampling channel leading to an alcohol-measuring device and a temperature sensor arranged in the connection area between the holder and the mouthpiece. The mouthpiece is designed as a coupling part in the connection area and the holder is designed as a mount. The temperature sensor is arranged as a temperature sensor at the holder in such a way that it detects the surface temperature of the coupling part.

The advantage of the present invention is essentially that the mouthpiece is designed such that the wall section, which is located in the overlapped area with the holder, is in contact with the inner side of the sampling channel and surrounds the temperature sensor located in the gas sample flow. A temperature difference between the holder and the mouthpiece can be clearly detected as a result, because the temperature sensor is directly surrounded by the wall section of the holder.

It is especially advantageous for the wall section to be designed as an outlet channel tubularly surrounding the temperature sensor. The outlet channel preferably has a length of about 8 mm and an internal diameter of about 4 mm.

It is especially advantageous to provide a second temperature sensor, which is arranged directly in the connection area between the holder and the mouthpiece and is in direct contact with the mouthpiece. It is thus possible to determine the surface temperature of the mouthpiece without an influence of the gas sample flow.

An advantageous process of determining a characteristic that is proportional to the temperature of the mouthpiece comprises the measurement of the maximum temperature drop with the temperature sensor, after the mouthpiece has been placed into its holder. This value is then used as a characteristic proportional to the temperature of the mouthpiece.

It is also advantageous to draw a small amount of air through the mouthpiece with the sampling pump of the breath alcohol-measuring device immediately after inserting the mouthpiece. The response behavior of the temperature sensors is markedly improved by the flowing air.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
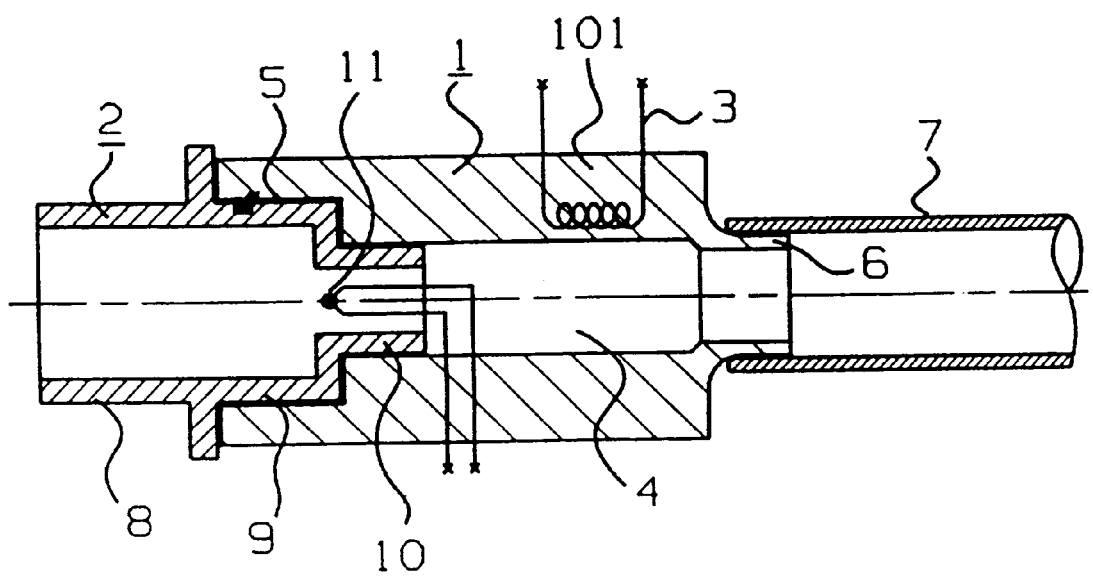
FIG. 1 is a cross sectional partially schematic view of a mouthpiece in its holder.

Referring to the drawings in particular, FIG. 1 shows the longitudinal section of a mouthpiece 2 inserted into a holder 1. The holder 1 has a housing body 101, which is made of a heat-conducting material and is provided with a heater 3 in order to heat a sampling channel 4 surrounded by the housing body 101 to a temperature of about 38° C. to 39° C. The holder 1 has a cylindrical mount 5 for the mouthpiece 2 at one end and, at the other end, a connection socket 6 for a sampling tube 7, which is connected to a breath alcohol-measuring device, not shown in FIG. 1. The mouthpiece 2, of an essentially cylindrical design, comprises a subject section 8, which is introduced into the mouth area of a subject, not shown in FIG. 1, and a coupling part 9, which is located inside the mount 5 of the holder 1. The coupling part 9 is joined by a tubular outlet channel 10, which has a length of about 8 mm and whose external diameter corresponds to the internal diameter of the sampling channel 4, which equals about 5 mm. A temperature sensor 11, which is arranged within the outlet channel 10 such that the gas sample released by the subject flows directly against it, is located within the sampling channel 4.

Figure 2:
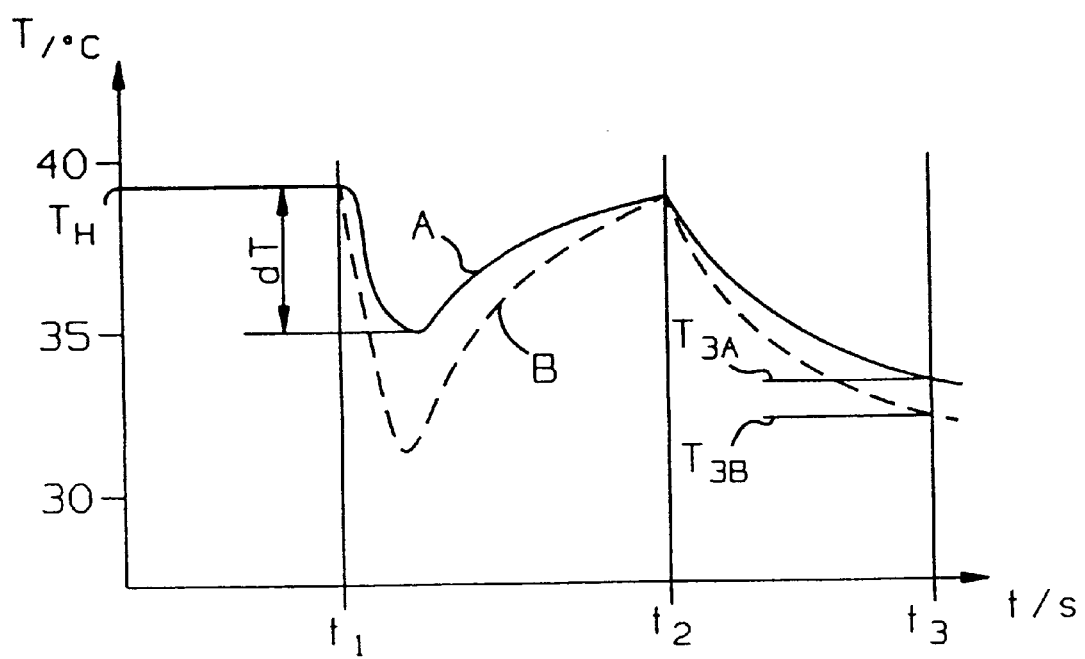
FIG. 2 is a diagram showing the change in the gas temperature measured in the area of the mouthpiece over time.

FIG. 2 shows the change in the temperature T measured with the temperature sensor 11 as a function of the time t before and after the gas sampling. The temperature T in ° C. is shown on the ordinate and the time t in sec on the abscissa. The holder 1 has been heated up to an operating temperature $T_H$ of about 39° C. There is no mouthpiece 2 within the mount 5 up to the time $t_1$, so that the temperature sensor 11 detects essentially the temperature of the housing body of the holder 1. A mouthpiece 2 is inserted into the mount 5 at the time $t_1$. The curves A and B indicate the change in the temperature T of mouthpieces 2, which was stored at different temperatures before, for times longer than $t_1$. Thus, the mouthpiece $T_L$ belonging to curve A has a storage temperature $T_L$ of 20° C., and the mouthpiece 2 belonging to curve B was stored at a temperature $T_L$ of 5° C. The temperature first decreases after the mouthpiece 2 has been inserted into the mount 5, because the temperature within the outlet channel 10 is measured with the temperature sensor 11. The greater the deviation of the temperature of the mouthpiece 2 from the temperature of the holder 1, the greater is the temperature drop. After the gradual heating of the outlet channel 10, the temperature T rises until the time $t_2$, until the temperature $T_H$ of the holder 1 has been reached. However, only the temperatures of the coupling part 9 and of the outlet channel 10 of the mouthpiece 2 increase during the time period between $t_1$ and $t_2$, while the subject part 8 is still at a lower temperature. This effect can be recognized in FIG. 2 at the time $t_3$. If the subject blows air with an assumed temperature of 35° C. into the mouthpiece 2 at the time $t_2$, the temperature measured with the temperature sensor 11 at the time $t_3$ drops to a value of $T_{3A}$ in the case of a mouthpiece 2 that was stored at a temperature $T_L$ of 20° C. (curve A). In contrast, the temperature $T_{3B}$ is obtained in the case of a mouthpiece 2 with the storage temperature $T_L$ of 5° C. (curve B). The temperature difference between $T_{3A}$ and $T_{3B}$ is an indicator of the distortion of the temperature measurement caused by the mouthpiece 2. Since the storage temperature of the mouthpiece 2 may be subject to great variations, e.g., between 0° C. and 40° C., this may lead to a measuring uncertainty of a few degrees Celsius during the temperature measurement. To correct this measuring uncertainty, the temperature of the mouthpiece 2 before the beginning of the measurement must be taken into account. The temperature $T_M$ of the mouthpiece 2, explained below on the basis of the example of curve A, can be estimated by means of the following empirical equation:

$$T_M = T_H - 3 \times dT.$$

in which $T_H$ is the temperature of the holder 1 before the insertion of the mouthpiece and dT is the temperature drop of curve A to the relative minimum after the insertion of the mouthpiece 2 into the mount 5.

The corrected temperature $T_K$ for the breath alcohol measurement, which would be obtained in the case of a mouthpiece 2 that would have been heated completely to the temperature $T_H$, can be calculated from the temperature $T_{3A}$ measured at the time $t_3$ by means of the following empirical equation:

$$T_K = T_{3A} + a \times (T_{3A} - T_M) - b \times (T_H - T_{3A}).$$

The value a depends on the volume of the breath gas blown into the mouthpiece 2 and equals 0.05 for a volume between 2.5 L and 5 L. The value of a is 0.1 up to a volume of 2.5 L.

Factor b describes the heating of the gas sample by the energy supplied from the holder 1 via the coupling part 9 and the outlet channel 10 to the breath gas sample. Factor b equals about 0.1 in this case. A corresponding correction can also be performed for curve B. The temperature drop dT was not shown in curve B for greater clarity.

Figure 3:
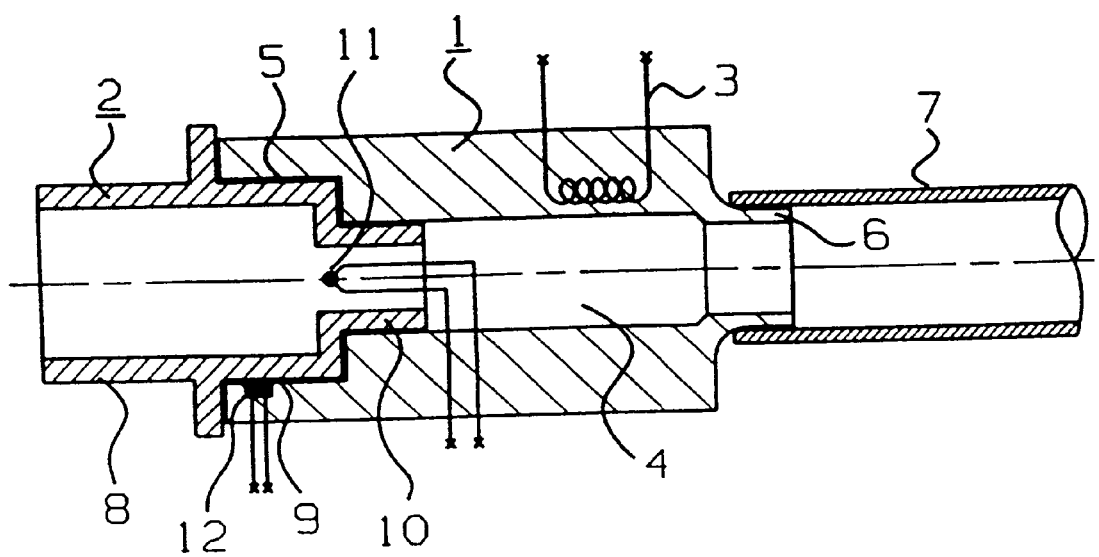
FIG. 3 is a cross sectional partially schematic view of an alternative embodiment of the device according to FIG. 1.

FIG. 3 shows an alternative embodiment, in which a temperature sensor 12 is arranged, unlike in the device according to FIG. 1, within the holder 1, in the connection area between the mount 5 and the coupling part 9. The surface temperature of the coupling part 9 can be directly measured with the temperature sensor 12. The temperature sensor 12 is located at the inner wall of the mount 5. The storage temperature of the mouthpiece can be determined from the temperature change measured with the temperature sensor 12, which change occurs upon the insertion of the mouthpiece 2 into the holder 1, without the measurement being influenced by the gas present in the sampling channel 4. The temperature of the gas sample is measured with the temperature sensor 11.

The process determines a characteristic proportional to a temperature of the mouthpiece as discussed above. The process includes the steps of:

measuring a first temperature $T_H$ with the temperature sensor before the mouthpiece has been received by the holder;

determining a maximum temperature drop dT compared with the first temperature $T_H$ after the mouthpiece has been received by the holder; and using the temperature drop dT as a characteristic proportional to the temperature of the mouthpiece.

A small amount of air may be drawn through the mouthpiece with a sampling pump 18 of the breath alcohol-measuring device 16. This should take place immediately after the mouthpiece is received by the holder.

Figure 4:
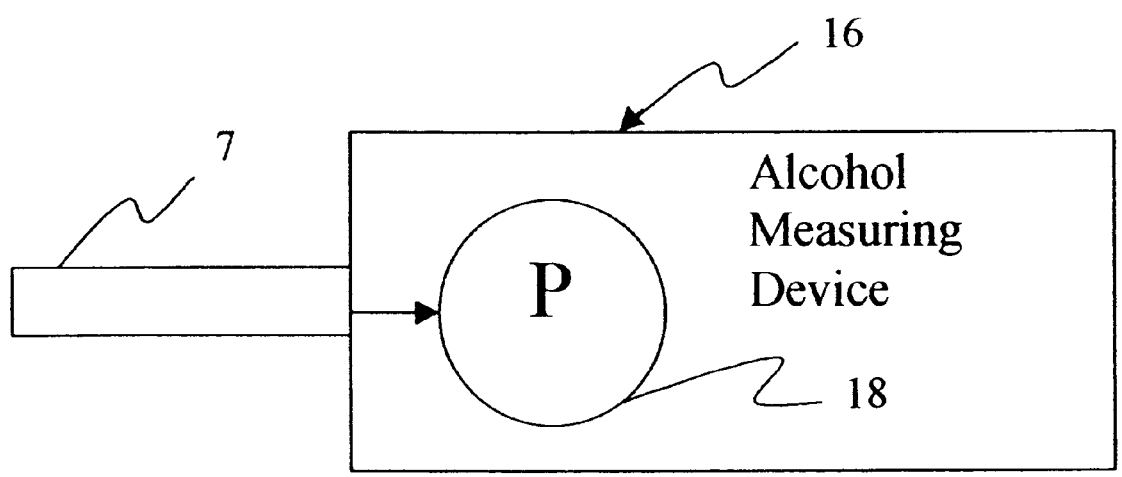
FIG. 4 is a schematical view of a breath alcohol-measuring device connected to a sampling tube.

FIG. 4 shows the breath alcohol-measuring device generally designated 16 connected to the sampling tube 7. The pump 18 is shown which may be used as noted above.

While specific embodiments of the invention have been shown and described in detail to illustrate the application of the principles of the invention, it will be understood that the invention may be embodied otherwise without departing from such principles.

What is claimed is:

1. A mouthpiece holder and alcohol measuring device combination, the combination comprising:

a mouthpiece;

a breath alcohol-measuring device;

a holder receiving portion which receives the mouthpiece and has a sampling channel leading to the breath alcohol-measuring device;

a temperature sensor arranged in a connection area adjacent to the holder and adjacent to the mouthpiece, said temperature sensor being arranged in said sampling channel with a wall section of said mouthpiece covering an inner wall of said sampling channel at least partially in an area of said temperature sensor;

temperature correction means associated with said breath alcohol-measuring device for providing a corrected temperature measurement signal from said temperature sensor based on a sensing of the temperature in said sampling channel before the mouthpiece is connected and a sensing of the temperature in said sampling channel after the mouthpiece is connected to provide an indication ofbreath temperature measurement distortion caused by said mouthpiece; and another temperature sensor, said mouthpiece having a coupling part in said connection area and said holder including a mount at said connection area with said connection area in said mount defining a mouthpiece holder interface, said another temperature sensor being arranged at said mouthpiece holder interface positioned to detect a surface temperature of said coupling part.

2. The combination in accordance with claim 1, wherein said wall section is an outlet channel of said mouthpiece tubularly surrounding said temperature sensor.

3. The combination in accordance with claim 1, wherein said another temperature sensor is arranged in the area of the inner wall of the said mount.

4. A device according to claim 1, further comprising: a heater associated with said holder for preheating the sampling channel to a predefined temperature.

5. A device according to claim 1, further comprising: a heater associated with said folder for preheating the sampling channel to a predefined temperature.

6. A process for determining a characteristic proportional to a temperature of a mouthpiece and holder combination, the combination including a holder receiving portion which receives the mouthpiece and has a sampling channel leading to a breath alcohol-measuring device and a temperature sensor, the process comprising the steps of:

arranging the temperature sensor in said sampling channel in a connection area adjacent to the holder and the mouthpiece;

arranging a wall section of the mouthpiece in said sampling channel covering an inner wall of the sampling channel at least partially in an area of said temperature sensor;

measuring a first temperature $T_H$ with the temperature sensor before the mouthpiece has been received by the holder;

determining a maximum temperature drop dT compared with the first temperature $T_H$ after the mouthpiece has been received by the holder; and using the temperature drop dT as a characteristic value proportional to the temperature of the mouthpiece.

7. The process in accordance with claim 6, wherein a small amount of air is drawn through the mouthpiece with a sampling pump of the breath alcohol-measuring device immediately after the mouthpiece is received by the holder.

8. A process for measuring breath alcohol, the process comprising the steps of:

providing a mouthpiece;

providing a breath alcohol-measuring device;

providing a holder receiving portion which receives the mouthpiece and has a sampling channel with an inner wall arranging a temperature sensor in said sampling channel;

arranging a wall section of the mouthpiece in said sampling channel covering said inner wall of said sampling channel in an area of the temperature sensor;

measuring a first temperature $T_H$ with the temperature sensor before the mouthpiece has been received by the holder;

measuring a second temperature with the temperature sensor for determining a maximum temperature drop dT compared with the first temperature $T_H$ after the mouthpiece has been received by the holder; and using the temperature drop dT as a characteristic value proportional to the temperature of the mouthpiece for determining the temperature of the gas sample blown by a subject for breath alcohol measurement.

9. The process in accordance with claim 8, further comprising the steps of drawing a small amount of air through the mouthpiece with a sampling pump of the breath alcohol-measuring device immediately after the mouthpiece is received by the holder for determining the maximum temperature drop dT.

10. The process in accordance with claim 8, further comprising heating the holder receiving portion to provide a predetermined initial sampling channel temperature.

* * * * *